United States Patent
Gilmour et al.

(10) Patent No.: US 7,758,527 B2
(45) Date of Patent: Jul. 20, 2010

(54) ORTHOTIC DEVICE AND SEGMENTED LINER

(75) Inventors: Robert Gilmour, Waiheke Island (NZ); Michael Skahan, Vista, CA (US); Kevin Lunau, Valley Center, CA (US)

(73) Assignee: VQ Orthocare, Irvine, CA (US)

( * ) Notice: Subject to any disclaimer, the term of this patent is extended or adjusted under 35 U.S.C. 154(b) by 417 days.

(21) Appl. No.: 10/591,966

(22) PCT Filed: Mar. 10, 2005

(86) PCT No.: PCT/US2005/008010

§ 371 (c)(1),
(2), (4) Date: Sep. 7, 2006

(87) PCT Pub. No.: WO2005/087148

PCT Pub. Date: Sep. 22, 2005

(65) Prior Publication Data

US 2007/0197946 A1    Aug. 23, 2007

(30) Foreign Application Priority Data

Mar. 10, 2004  (NZ) ..................................... 531705

(51) Int. Cl.
*A61F 5/00* (2006.01)
(52) U.S. Cl. .......................................... 602/23; 602/26
(58) Field of Classification Search .............. 602/5, 602/13, 16, 26–27, 23; 128/882
See application file for complete search history.

(56) References Cited

U.S. PATENT DOCUMENTS

| | | | |
|---|---|---|---|
| 4,872,448 A | 10/1989 | Johnson et al. | |
| 4,938,207 A | 7/1990 | Vargo et al. | |
| 5,230,697 A | 7/1993 | Castillo et al. | |
| 5,277,698 A * | 1/1994 | Taylor | 602/26 |
| 5,288,287 A | 2/1994 | Castillo et al. | |
| 5,316,547 A * | 5/1994 | Gildersleeve | 602/26 |
| 5,542,911 A * | 8/1996 | Cassford et al. | 602/26 |
| 5,645,524 A * | 7/1997 | Doyle | 602/16 |
| 6,110,135 A | 8/2000 | Madow et al. | |
| 2003/0187375 A1 | 10/2003 | Gaylord | |

FOREIGN PATENT DOCUMENTS

DE    20116887    2/2002

* cited by examiner

*Primary Examiner*—Michael A. Brown
(74) *Attorney, Agent, or Firm*—Sheppard Mullin Richter & Hampton LLP

(57) ABSTRACT

An orthotic device is provided having a support member (22, 25) adapted to be secured to a body portion of a user and a resilient liner (46) connected to a side of the support member adjacent the body portion of the user. The support member can be malleable to conform to the user's body. The liner has a plurality of discrete liner segments (49), at least one adapted to conform to body of the user. The liner segments can be removably attached to the support member, and can be adjustable in shape and/or size. The liner segment can be a pair of individually adjustable segment portions to provide adjustable shape, and either of the portions can be inflatable to provide adjustable size. The liner segment can include an electrode portion (58) to impart therapeutic stimulation to an associated body portion and can include a micro-porous waterproof cover material contacting the body portion of the user.

15 Claims, 8 Drawing Sheets

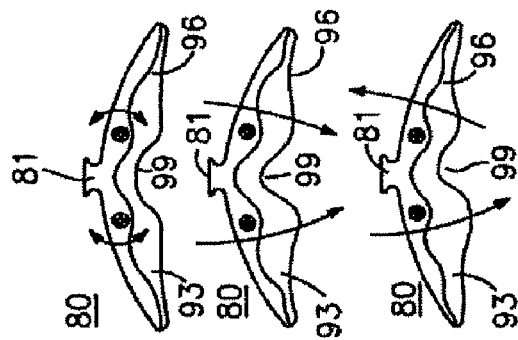
FIG. 11
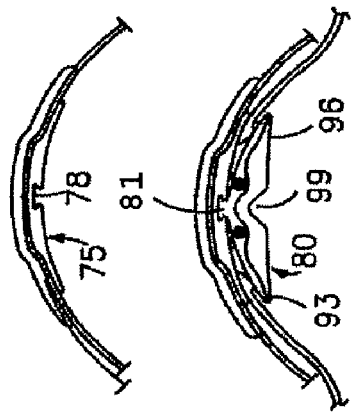
FIG. 9
FIG. 10
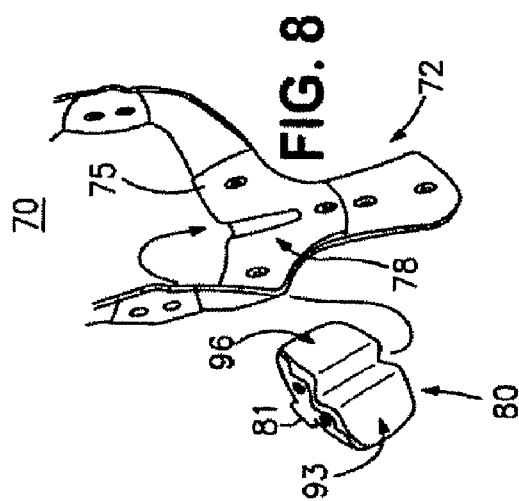
FIG. 8
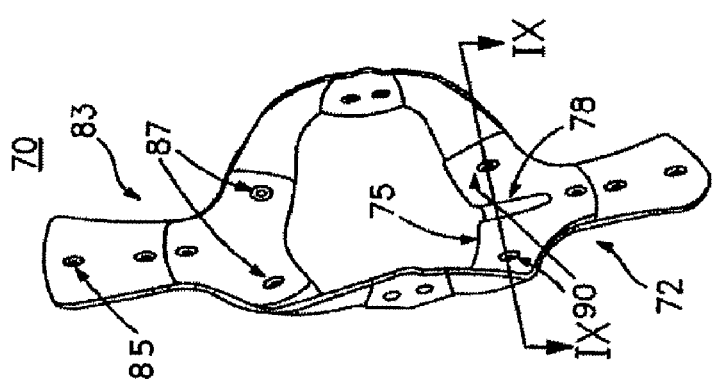
FIG. 7

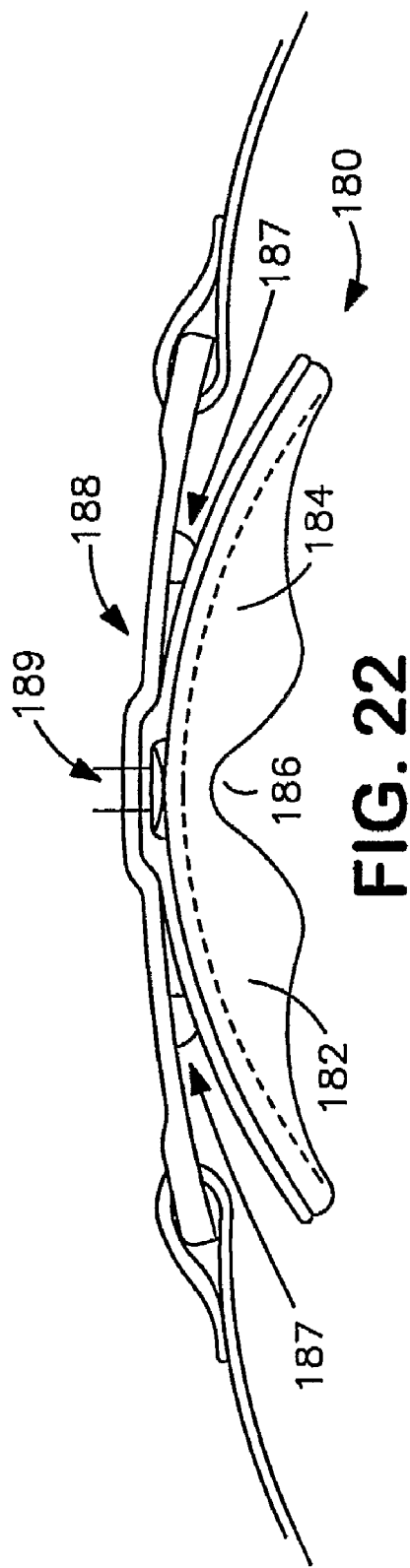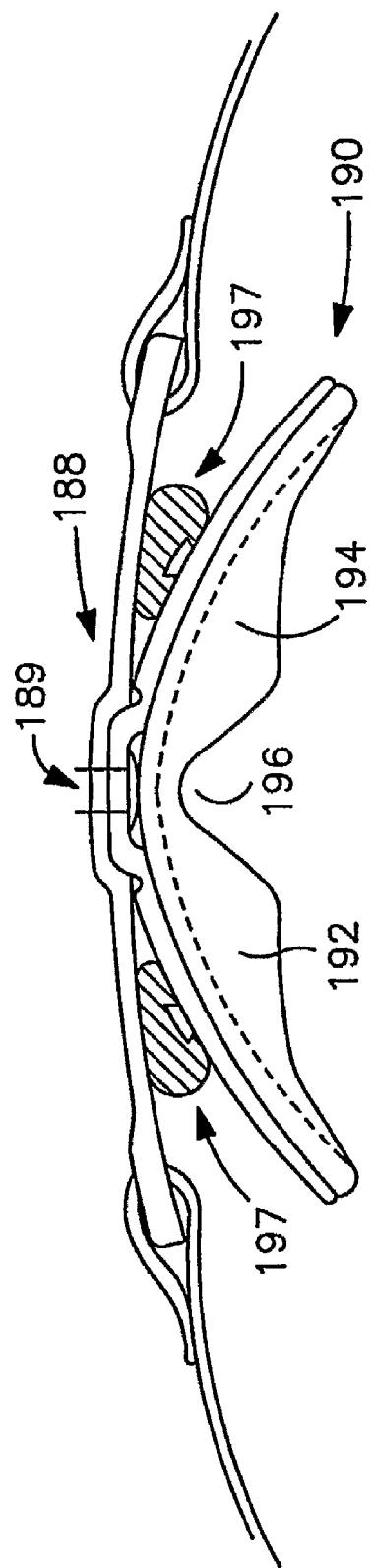

ORTHOTIC DEVICE AND SEGMENTED LINER

BACKGROUND OF THE INVENTION

1. Field of the Invention

This invention relates to orthotic devices, and in particular to a knee brace having a resilient, conforming interface between the brace and the users leg.

2. Description of the Prior Art

Orthotic devices generally include a substantially rigid biomechanical element that forms the basis of the skeletal support that is required for the majority of these devices, which include braces, supports and splints.

The human knee generally comprises an articulated joint between the thigh and the calf muscles that supports the weight of the human body while the person is standing, walking or running. The knee joint is primarily held together by four ligaments; namely, the anterior and posterior cruciate ligaments and the medial and lateral collateral ligaments. The knee joint can be overly weakened by injuries arising out of cartilage damage and ligament strain, which may be caused, by sports injuries, as well as from everyday exercising, or physiological problems such as osteoarthritis. Thus, the human knee is subjected to a variety of stresses and strains particularly during running and jumping movements. Athletes, in particular, are apt to incur a knee injury as a result of a blow to the knee or to a twisting of the knee, which can commonly occur in various contact sports or high stress sports, such as skiing.

There are a variety of knee braces available on the market or through healthcare providers. These range from braces that tend to totally immobilize the knee to flexible elastic bandages that are intended to provide some flexibility while eliminating lateral movement of the ligaments that support the knee. Some of these are intended to be worn as a relatively permanent device for long-term wear or braces that are intended to be worn for a short period of time during overly strenuous for a short period of time for a weakened knee. The braces have as their primary object to allow for pivoting the knee while preventing any unnatural movement, which may aggravate the knee ligaments. While the braces are intended to allow for a natural movement of the knee joint while a person undergoes walking, running, jumping, skating, various other athletic activities, they are intended also to prevent sudden movement of the upper and lower legs to one side or the other and to prevent twisting or rotation of the lower leg relative to the upper leg about the vertical axis.

Typically, the knee braces are held in place by flexible straps, which wrap about the user's thigh and calf above and below the knee, respectively. In this manner, the rigid hinge of the knee brace remains positioned on either side of the user's knee so as to mimic the hinged joint of the knee. However, it is not uncommon for the user's bodily motions to cause the flexible straps to move relative to the person's leg, thereby misaligning the knee brace with respect to the knee. This movement of the brace straps with respect to the user not only cause misalignment and therefore misapplication of the orthotic device, but also cause irritation of the user's skin by this unintended rubbing.

A problem with orthotic devices is that they must engage effectively with soft tissue in order to provide the desired support. In many parts of the body the soft tissue will move, for example by expanding or contracting as result of muscle movement. As a soft tissue changes shape, parts of the skin lose contact with the liner of the orthotic device. This reduced contact with the liner can cause the orthotic device to lose position, or move relative to the user and therefore become ineffective. The only way of overcoming this problem with existing devices is to tighten the device. This causes discomfort, prevents the skin from breathing, and can irritate the skin about the edges of the device and the liner.

The objective of any rigid knee brace is to exert a predictable force on the user's underlying skeleton. In particular, the objective is to exert a force on the tibia with respect to the femur in the user's body mass above the knee. By definition, knee braces are applied to soft tissue lying between the brace and the user's skeleton. The rigid element may include some form of liner that contacts the body of the user. The liner may have an outer fabric that is designed to contact the user's skin directly or, alternatively, to engage with clothing that a user may be wearing about the pat of the anatomy to which the orthotic device is to be attached. Soft tissue is mobile and moves in a cycle corresponding to a user's gait, whether it be through running, walking or other physical movement common to the human knee. The most mobile soft tissue is the quadriceps mechanism lying in front of the femur in the anterior thigh region. The central reference point for a knee brace is the knee joint line. In construction, an orthotic device such as a knee brace would use a joint mechanism, which mimics the movement of the joint to be supported, such as the knee, which is not just a simple hinge. Since each user's body shape is unique, the interface between the orthotic device and the user's leg cannot be predetermined in the manufacture of such a device.

What is needed then, is an orthotic device which can more readily conform to a particular user's leg, such that the straps fit snugly, yet comfortably, about the user's leg adjacent the knee, but yet provide the adequate support so as to prevent relative movement of the knee brace with respect to the knee so that the brace provides its desired function.

With a damaged knee joint, it is also not uncommon for the user to experience pain within the muscle surrounding the knee, since those muscles must now try to support the weakened knee in the absence of the normal strength provided by the now damaged ligaments. It would be advantageous if a knee brace could also provide therapeutic relief to the user's muscles while also providing the support needed for the damaged knee.

There is a need for an orthotic device, or apparatus for such a device, which will at least go some way toward overcoming disadvantages of existing constructions, or which will least provide the public with a useful alternative.

SUMMARY OF THE INVENTION

Accordingly in one aspect the invention broadly provides an orthotic device having a substantially rigid support, such as a cuff assembly, and a liner arrangement for provision between the support and the body of a user, the liner arrangement comprising a plurality of segments, such as spaced protuberances, which provide a snug fit for the orthotic device against a body portion of the user.

Preferably each segment, or protuberance, comprises a distinct, discreet element attached directly or indirectly to the support.

Alternatively some or all of the protuberances are interconnected and together attached directly or indirectly to the support.

Preferably each protuberance comprises a segment or series of segments, which may be individually connected or disconnected (either directly or indirectly) to or from the support.

Preferably each segment comprises a material having properties of resilience covered with a sheet material. Preferably the sheet material comprises a material sold under the trade name DRY-X.

Preferably the segments are arranged depended upon the anatomy about which the orthotic device is to the fixed.

Preferably selected properties of each segment may be selected by a user to improve engagement of the orthotic device with the anatomy of the user, such properties including without limitation shape, size and resilience.

Preferably the segments may contain or include materials such as solid pockets (for example water, gel, or air, and can be inflated/deflated pneumatically.

Alternatively to addition, the segments may include electrodes to provide electrophysical modality such as muscle stimulation or transcutaneous electro-nerve stimulation (TENS).

Preferably a liner, or segments thereof, can be adjustable in regard to position and angle of the segments on the support.

Preferably the segments can comprise a pair of discreet segment portions which can be independently adjustable in various ways, including relative to each other, to improve engagement of the support with the anatomy of the user.

Further respect to the invention will become apparent from the following description, which is given by way of example only.

BRIEF DESCRIPTION OF THE DRAWINGS

Various other objects, features and advantages of the present invention will become readily apparent by reading the following description in conjunction with the drawings, which are shown by way of example only, wherein:

FIG. 7 is a perspective view of an orthotic device adapted for receiving a segmented tibial liner element;

FIG. 8 is a view partially in section of the orthotic device in FIG. 7 illustrating attachment of the segment and tibial liner element;

FIG. 9 is a cross section view taken through line IX-IX in FIG. 7;

FIG. 10 is a cross section view similar to FIG. 9 and also illustrating attachment of the segmented tibial liner;

FIG. 11 illustrates a preferred embodiment of a segmented active tibial management liner;

FIG. 22 is a cross section view showing a segmented tibial liner receptacle plate in and alternative manner of attaching a segmented tibial liner; and FIG. 23 is a cross section view similar to FIG. 22, showing a still further embodiment of a manner of attaching a segmented tibial liner.

DETAILED DESCRIPTION OF THE PREFERRED EMBODIMENTS

Figure 1:
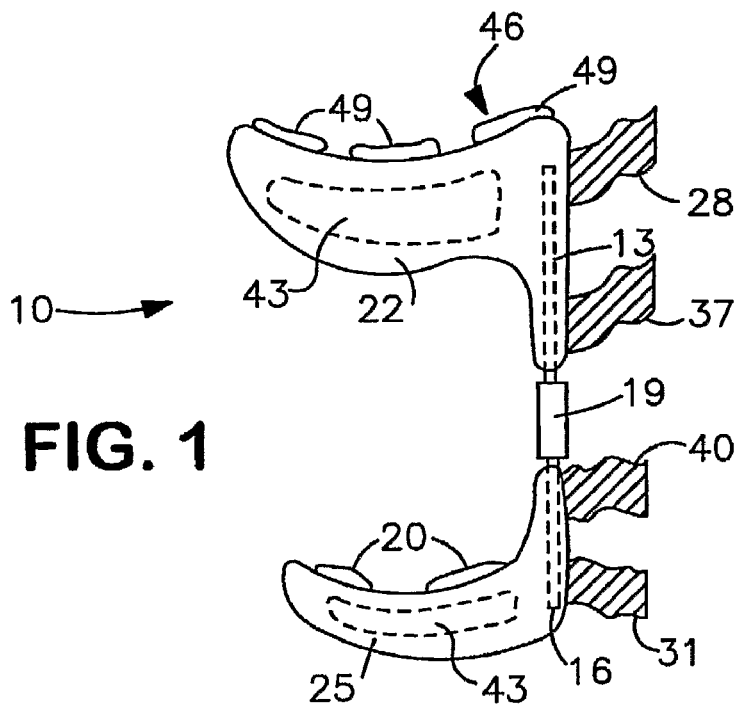
FIG. 1 is a front elevation of a knee brace according to the present invention.
Figure 2:
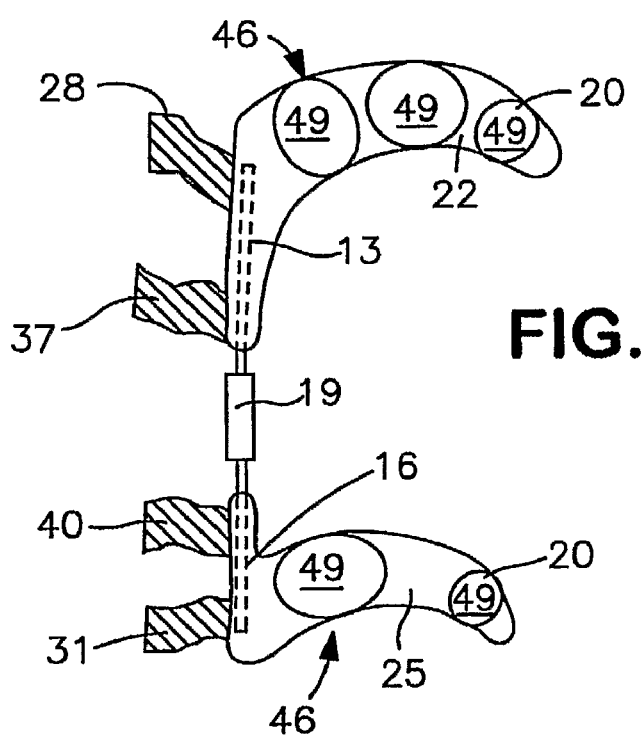
FIG. 2 is a rear elevation of the brace of FIG. 1.
Figure 3:
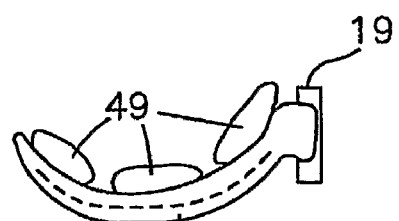
FIG. 3 is a partial plan view of the brace of FIG. 1.

Referring now to the drawings in detail, wherein like reference characters refer to like elements, there is shown in FIG. 1 a knee brace 10 according the present invention. The invention will be described with reference to a knee brace; however, it will be understood that the invention is also applicable to other orthotic devices such as an ankle or wrist brace, and other devices for relieving pain in any body portion of the user. Although this invention will be described by way of example and with reference to preferred embodiments thereof, it is to be understood that modifications or improvements may be made thereto without departing from the scope or spirit of the invention. It should be noted that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be included within the present invention.

Referring to FIG. 1, a knee brace 10 is shown having a biomechanical support comprising two substantially rigid arms, 13 and 16, which are joined together by a hinge assembly 19. Connected to the rigid arms are upper and lower structures 22 and 25, respectively which, together with straps 28 and 31 are used to form a primary engagement with the user's leg above and below the knee 34. This engagement can be augmented by further straps 37 and 40. The hinge assembly 19 has a predetermined range of movement corresponding to the desired range of flexion/extension of the knee of the user. The upper and lower support structures 22, 25 are generally referred to as cuffs.

The upper cuff 22 is adapted to be secured to the user's thigh (femur) and the lower cuff 25 is adapted to be secured to the lower leg or calf (tibia). In this way the hinge assembly 19 is placed adjacent the axis of the user's knee joint, thereby allowing the knee brace 10 to substantially mimic the bending of the user's knee as the user goes about his or her otherwise normal activities. In the preferred embodiments, upper and lower cuffs 22, 25 comprise adaptive support structures that are constructed from a semi-rigid material such as a thermoplastic elastomer or a thermoplastic rubber.

Furthermore, the preferred embodiments may include a rigid material 43 that is integrally moulded into upper and lower structures 22, 25, or is alternatively fixedly attached to the strictures. Rigid material 43 has a greater rigidity than the semi-rigid material from which upper and lower structures 22, 25 are moulded, and is preferably malleable. In the preferred embodiments, rigid material 43 comprises a sheet aluminum material which has an appropriate thickness (for example, on the order of about 1-2 two millimeters thick), or other deformable metal, so that it may be easily shaped by the user using his or her hands to assist the adaptive material from which the structures 22, 25 are manufactured to generally conform to the portion of the anatomy to which the device is to be attached.

Attached directly or indirectly to the upper and lower cuffs 22, 25 is a liner arrangement 46, which may take a variety of different forms. In the most preferred embodiments illustrated in the figures, the liner arrangement 46 takes the form of a plurality of discreet segments 49. Each segment 49 preferably comprises a resilient material, which may be formed by moulding for example, cutting or otherwise shaping an appropriate material. Alternatively, in the most preferred embodiments each segment 49 comprises a material such as a soft resilient foam and an outer layer of material which is intended to contact human skin, such as material sold under the trade name DRY-X. This material is preferred for its property of combining a highly durable nylon material with a micro-porous waterproof and breath-able coating, which allows perspiration of the user to escape through the fabric while preventing moisture from entering the brace so as to provide a comfortable feel for the user of the brace 10.

Each segment 49 may also have properties of resilience provided by a fluid, such as air or water, or other substances such as gels. The segments 49 may include a fluid or gel which can be heated or cooled yet is still resilient and conforming, so as to provide an additional therapeutic benefit to the user. Because of their resilience, the segments 49 adapt to the particular leg shape and musculature of the user. This enables the knee brace 10 to accommodate a variety of muscular shapes and sizes, as the resilient segments 49 readily conform to the user's thigh and calf as the cuffs 22, 25 are secured about the user's leg. The brace 10 can be made snug to the user's leg without having to over-tighten the straps 28, 31, 37 and 40. Moreover, the DRY-X material, or other breathable fabric, prevents excess moisture or sweating of the user's leg between the skin and the brace.

The segments 49 may be engaged with upper and lower upper and lower cuffs 22, 25 by providing those structures with a selected lining, such as a hook and loop fastener arrangement, commonly referred to as "VELCRO." One half of the VELCRO material is provided on the rear portion of each segment 49 and can then be engaged with the other half VELCRO on the upper and lower cuffs 22, 25 so that the segments can be secured in the desired position. This construction has a further advantage that the segments may be repositioned depending upon the requirements of the user. Furthermore, segments of a number of different shapes and sizes having different properties (for example varying properties of resilience or hardness) may be provided and the user may substitute segments or rearrange the location of segments so that a comfortable and effective fit is achieved.

Figure 4A:
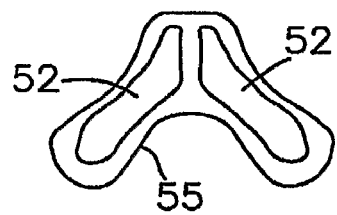
FIG. 4, consisting of FIGS. 4A and 4B, is a plan view and side elevation, respectively of a liner element of the present invention.
Figure 4B:
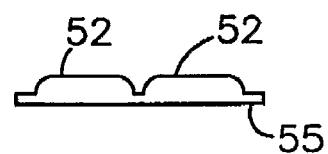
Figure 5A:
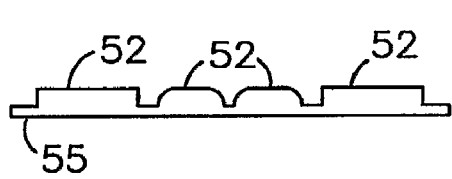
FIG. 5, consisting of FIGS. 5A and 5B, is a plan view and side elevation, respectively of an alternative embodiment of the liner element.
Figure 5B:
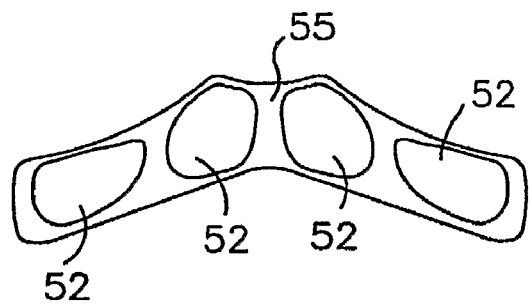

As another alternative, the segments may advantageously be linked together. For example, in FIGS. 4 and 5 segments 52 are illustrated as being interconnected by being placed on a substantially planar substrate 55. As can be seen, each segment 55 protrudes, so that when a rear surface of substrate 55 is affixed to support structure 22, 25 for example, the segments 55 make contact with the body of the user. As discussed above, the segments 55 may also be provided with varying properties, for example varying size (including varying height of protrusion), varying properties of resilience or support, and varying position.

The design of the segments can also be such as to facilitate skeletal grip, quite apart from grip to soft flesh or pure arrangement for user comfort. Therefore, for example the interconnected segments illustrated in FIGS. 4 and 5 may be provided in a knee brace 10 to provide enhanced skeletal grip, for example gripping the tibia.

Figure 6A:
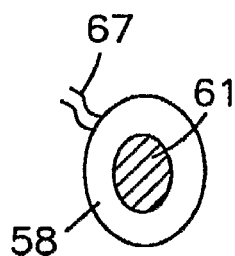
FIG. 6, consisting of FIGS. 6A and 6B, is a front elevation and rear elevation, respectively, of a liner segment having electrophysical modality according to the present invention.
Figure 6B:
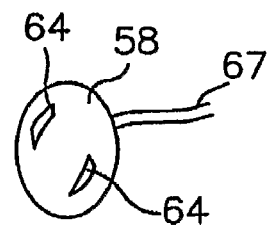
Figure 12:
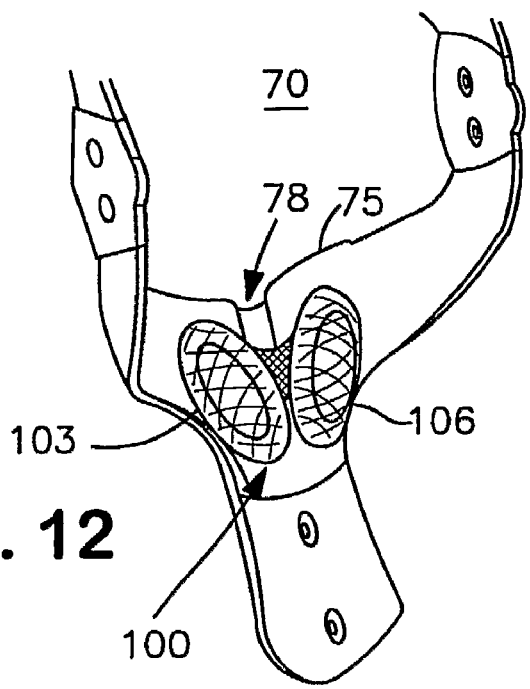
FIG. 12 is a view partially in section of the orthotic device in FIG. 7 and illustrating an alternative embodiment of a segmented tibial liner.

Turning to FIG. 6, yet another application of the invention can be described with reference to segment 58 which on a reverse side can include a VELCRO attachment 61 to enable the segment 58 to be connected to the support structure 22, 25 of the orthotic device 10, as described above. However, on the side of the segment 58 that contacts the body of the user, the segment includes one or more electrodes 64 which are supplied with electrical energy by one or more conductors 67. The conductors 67 are connected to an electrical source (not shown) such as a portable and lightweight battery pack that can easily be carried on the user's body. By supplying electrical energy in the desired form, the segment 58 can provide Electrophysical Modality such as muscle stimulation, for example stimulating quadriceps muscles in the user's knee, and provide pain relief such as that commonly known as TENS. Each segment (or selected segments) may include one electrode 64, which forms a circuit with another electrode (or electrodes) on other segments 58.

TENS is typically produced through high frequency electrical stimulation of the nerve, which disrupts the pain signal so that the pain is no longer felt. Although the exact mechanism is not yet known, it is believed that TENS works by two different ways. First, electrical stimulation of the nerve fibers can block a pain signal from being carried to the brain. If the signal is blocked, pain is not perceived by the user. Second, the human body has its own mechanism for suppressing pain; it does this by releasing natural chemicals, called endorphins, in the brain which act as analgesics. TENS may activate this mechanism. By using these electrical pulses to stimulate the nerve endings at or near the site of the pain, the user feels diminished pain that is replaced by a tingling or massage-like sensation. The electrical power and circuitry for providing the TENS stimulation can be provided in a small and relatively lightweight package (not shown) which can be worn on the users hip, or directly on the orthotic device, depending on its complexity and size. Thus, the orthotic device 10 of the present invention not only provides the desired support for the user's otherwise weakened knee, but also provides a therapeutic benefit to the user's leg muscles.

A key purpose segmentation is to enhance functionality. Segmentation enables a degree of customization of the interface of the orthotic device with an individual's anatomy so as to achieve better grip and fit. Each segment of the liner can be viewed as an individual component, and after considering the surface anatomy and characteristics of the tissue interface, customization of a segment provides solutions to variable shape, tissue turgor, soft tissue mobility, and the like. Additional solutions are the incorporation electrodes for physiological modalities, e.g., TENS.

As will be described in more detail hereinafter with respect to FIGS. 7-23, an adjustable liner, or adjustable portions, e.g., segments thereof, can provide multiple solutions to the problem of different anatomy profiles. In general, segments of an adjustable liner can be configured to enhance fit, in effect being customizable for a particular individual. Embodiments of the adjustable liner can include segments thereof which are individually adjustable to suit specific activity levels in individual anatomy to insure optimum control of movement in rotation of portions of the anatomy.

FIGS. 7-23 illustrate certain such embodiments of the invention in the context of a practical example of an application for an adjustable liner according to the invention. Specifically, embodiments of the adjustable liner are illustrated as components of the tibial support member, or cuff, of a knee a brace which interfaces with the anterior border of the tibia (i.e., the shin). The purpose of such a brace is to hold the tibia in position and to prevent it from subluxing (i.e., slipping forward or back or to either side or rotating). To accomplish this purpose, maximum grip is desirable. There is a variety of anatomical shapes in any 4 Aug. 23, 2007 population group, and frequently a difference between male and female profiles in the anterior tibial border region. The adjustable liner, or adjustable segments thereof, utilized in the tibial region to provide, for example, adjustment for these differences is referred to occasionally hereinafter as an Active Tibial Management (ATM) system.

Although the following drawing figures illustrate, by way of example, such an adjustable liner, or adjustable segments thereof, specifically adapted for positioning in the orthotic device adjacent the tibia of a user; the application for an adjustable liner according to the invention is not limited to use in regard to only the tibia, but can be satisfactorily designed to be used with various other parts of the anatomy, and adjacent not only skeletal structure like the tibia, but also soft tissue. The adjustable liner, and particularly adjustable segment thereof, can be treated as an individual component, which can be individually designed, after considering the surface anatomy and characteristics of the specific tissue interface, to provide solutions to variable shape, tissue turgor, soft tissue mobility, and the like. As mentioned previously, electrodes for physiological modalities can also be incorporated.

Referring now to FIG. 7, an orthotic device 70 is illustrated wherein a lower portion 72 of the orthotic device is adapted to be located adjacent the tibia of a person's leg is shown having an ATM back plate 75 including a receptacle, or slot 78, to receive an adjustable tibial liner pad 80 via a rib 81 on the back surface of the adjustable liner 80. As can be seen in FIG. 7, the upper portion 83 of the orthotic device 70 can include an attachment point 85 for other adjustable and/or segmented liners or adaptive element attachments. In addition, upper attachment points 87 for a femoral proximal strap (not shown) and lower attachment points 90 for a gastrochnemius strap (not shown) can also be provided. The adjustable liner 80 can preferably comprise a pair of arm segments, or cams 93, 96, which define a tibial crest alignment groove 99 there between. Each cam segment 93, 96 can be individually adjustable in a variety of ways. In this manner, the cam segments 93, 96 can be manipulated to adjust the shape of the adjustable liner 80.

As shown better in FIGS. 8, 9 and 10, adjustable cams 93, 96 of the tibial liner 80 enable an individual, adjustable fit for specific activity levels and individual anatomy types to ensure optimal movement and rotation of the tibia. The individually adjustable cams 93, 96 enable adjustment on either side of the tibial crest 99 to ensure optimum fit and conformity to an individuals antimony.

FIG. 9 is a cross section view showing the receptacle, e.g., slot 78, in the ATM back plate 75, and FIG. 10 shows the adjustable tibial liner 80 secured against the ATM receptacle plate 75 with the rib 81 engaged in the slot 78.

Referring now to FIG. 11, the three views illustrate how the adjustable cams 93, 96 are adjustable in a plurality of different ways. As the upper most view shows each cam 93, 96 on opposite sides of the tibial crest 99, can be rotated forwards or backwards to adjust the fit. Additionally, as illustrated in the center view, both of the cams 93, 96 can be adjusted towards each other, or away from each other, to increase or decrease the pressure against the tibia as desired. Finally, the lower view illustrates how the cams 93, 96 can be adjusted to provide increased pressure on only one side of the tibia, to fit an individual's anatomy and to counteract rotation.

Figure 13:
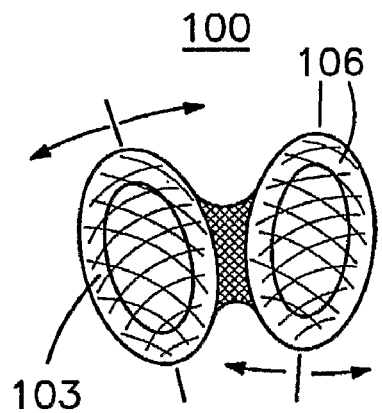
FIG. 13 illustrates an embodiment of a segmented active tibial management liner.
Figure 14:
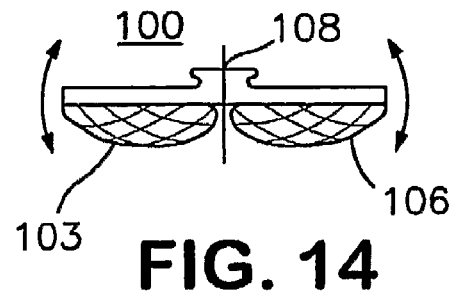
FIG. 14 is a top plan view of the segmental tibial liner element in FIG. 13.

FIGS. 12 through 15" illustrate a further embodiment of an adjustable tibial liner 100, in which the adjustable liner 100 can comprise a pair of pad segments 103, 106 which can be adjusted similarly to the cam segments 93, 96 in the previously described embodiment of the adjustable tibial liner 80. In this present embodiment, the adjustable tibial liner 100 can be secured to the ATM back plate 75 in the same fashion as the adjustable tibial liner 80 described previously, such as via a rib 108 received in the receptacle, i.e., slot 78, in the ATM back plate 75. Each pad segment 103, 106 can be adjusted in the ways illustrated in FIGS. 13-15. As shown in FIG. 13, each pad segment 103, 106 can be individually rotated (clockwise or counter-clockwise), either away from or towards each other. Alternatively, a single pad may be rotated in either such direction without adjustment of the other pad. FIG. 14 shows a second type of adjustment, toward or away from the tibia, which is common with the adjustable arm segments 93, 96 of the adjustable liner 80, as shown in FIG. 11.

Figure 15:
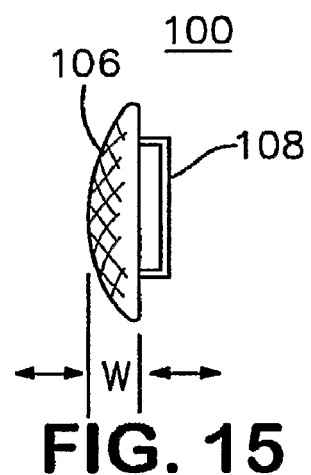
FIG. 15 is a side plan view of the segmented active tibial liner element in FIG. 13.

Referring to FIG. 15, the adjustable tibial liner 100 can additionally be designed such that each pad segment 103, 106 incorporates a pneumatic bladder, to enable each pad segment 103, 106 to expand or shrink. This enables increased control of the individual pressure of each pad segment 103, 106 to counteract tibial rotation, and to also provide a more customized fit relative to the individual's anatomy. As shown in FIG. 15, each pad 103, 106 has a certain thickness, and by provision of a pneumatic system for inflating and/or deflating each individual pad 103, 106, the width "W" of each pad 103,106 can thereby be increased or decreased to control the individual pressure each pad 103, 106 exerts on the tibia.

Figure 17:
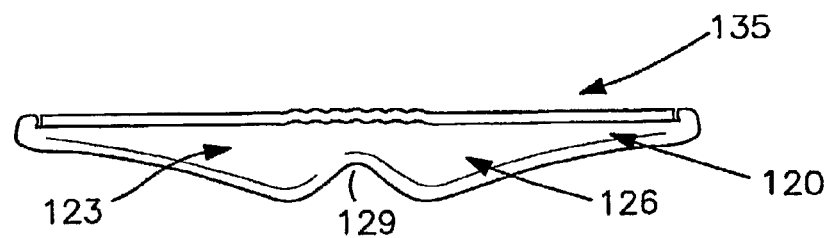
FIG. 17 is a top plan view of the segmented tibial liner in FIG. 16.
Figure 16:
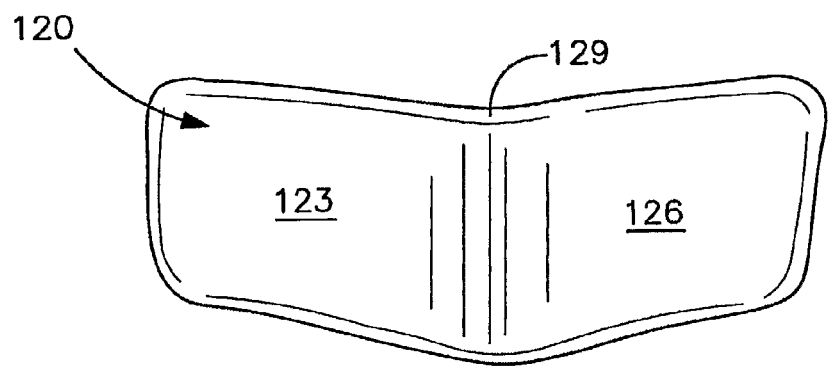
FIG. 16 is a front plan view of a segmented tibial liner.
Figure 18:
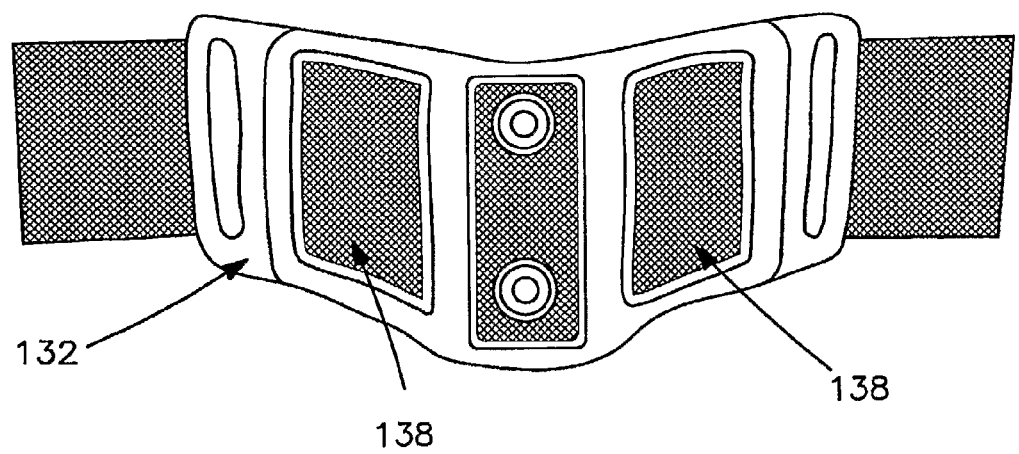
FIG. 18 is a front plan view of a segmented tibial liner receptacle plate, such as on an orthotic device as shown in FIG. 7.

Referring now to FIGS. 16, 17 and 18, a further embodiment of an adjustable tibial liner 120 is illustrated which can be similar to the adjustable tibial liner 80 in FIGS. 7-11. The tibial liner 120 includes cam segments 123, 126 which can be individually adjustable, and which define a tibial crest groove 129 there between. A difference is that the adjustable tibial liner 120 in FIG. 16 is attachable to an ATM back plate 132, such as shown in FIG. 18, via a hook and loop fastener system, e.g., VELCRO. As shown in FIG. 17, a layer 135 of VELCRO material can be provided on the back surface of the adjustable liner 120 and can mate with cooperating portions 138 of VELCRO provided on the ATM plate 132 shown in FIG. 18.

Figure 19:
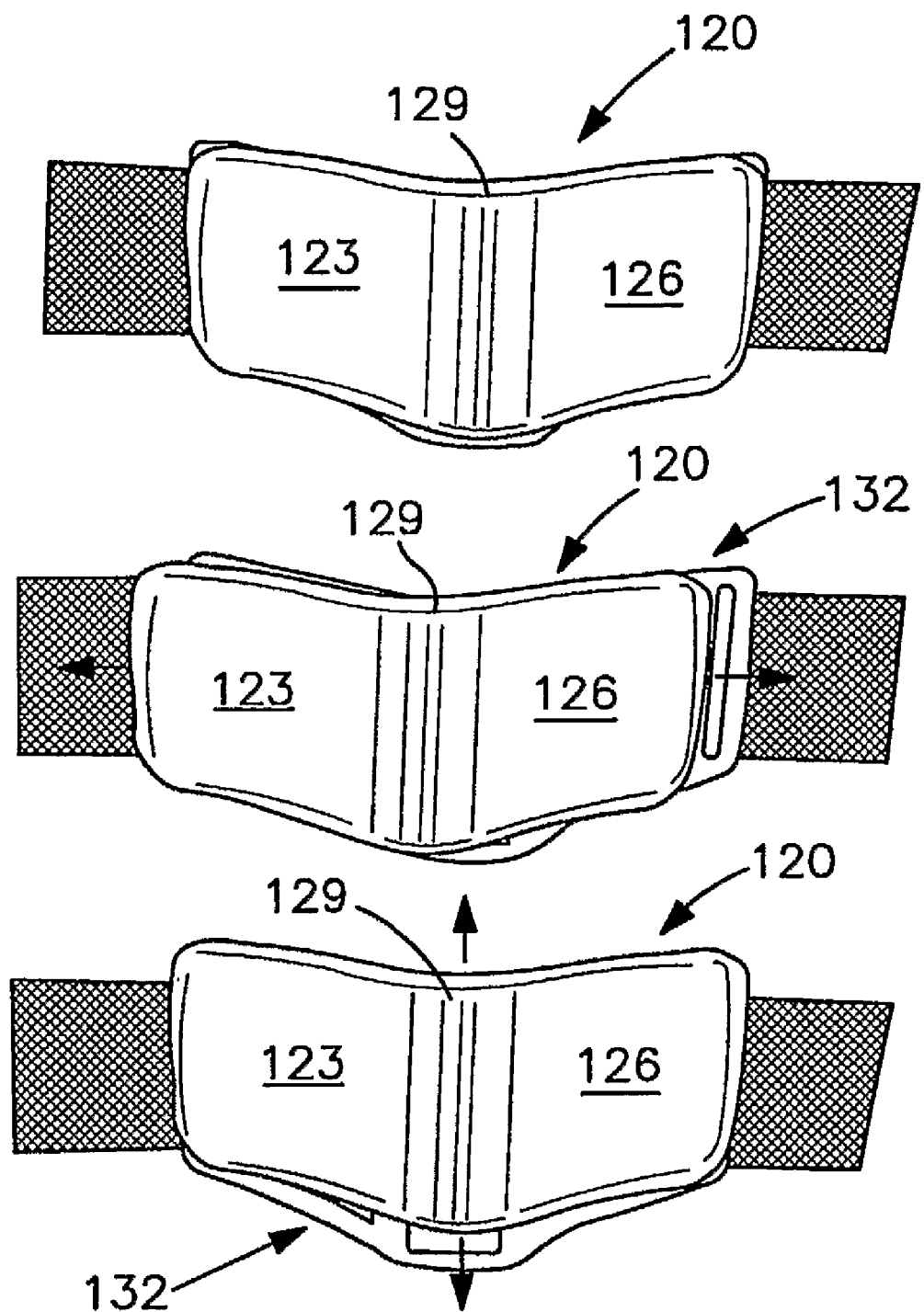
FIG. 19 illustrates variable attachment positions for the segmented tibial liner as shown in FIGS. 16 and 17.

Referring to FIG. 19, the three views show that the adjustable tibial liner 120 can be easily attached at a number of different positions on the ATM plate 132, as enabled by the VELCRO attachment system. For example, the adjustable liner 120 can be centered on the ATM plate 132 as shown in the top view, or can be offset laterally (left to right) as shown in the center view, or can be offset vertically (up and down) as shown in the bottom view. Additionally, any combination of lateral and vertical offset is also possible.

Figure 21:
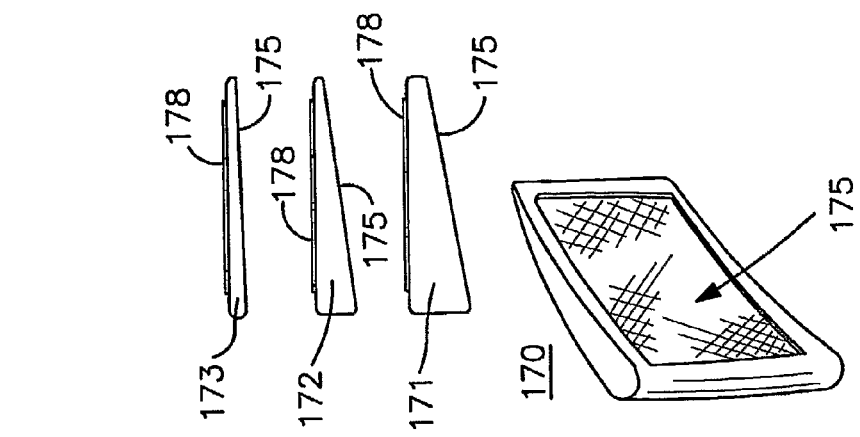
FIG. 21 illustrates an embodiment of a chock for use with the segmented tibial liner in FIG. 20.
Figure 20:
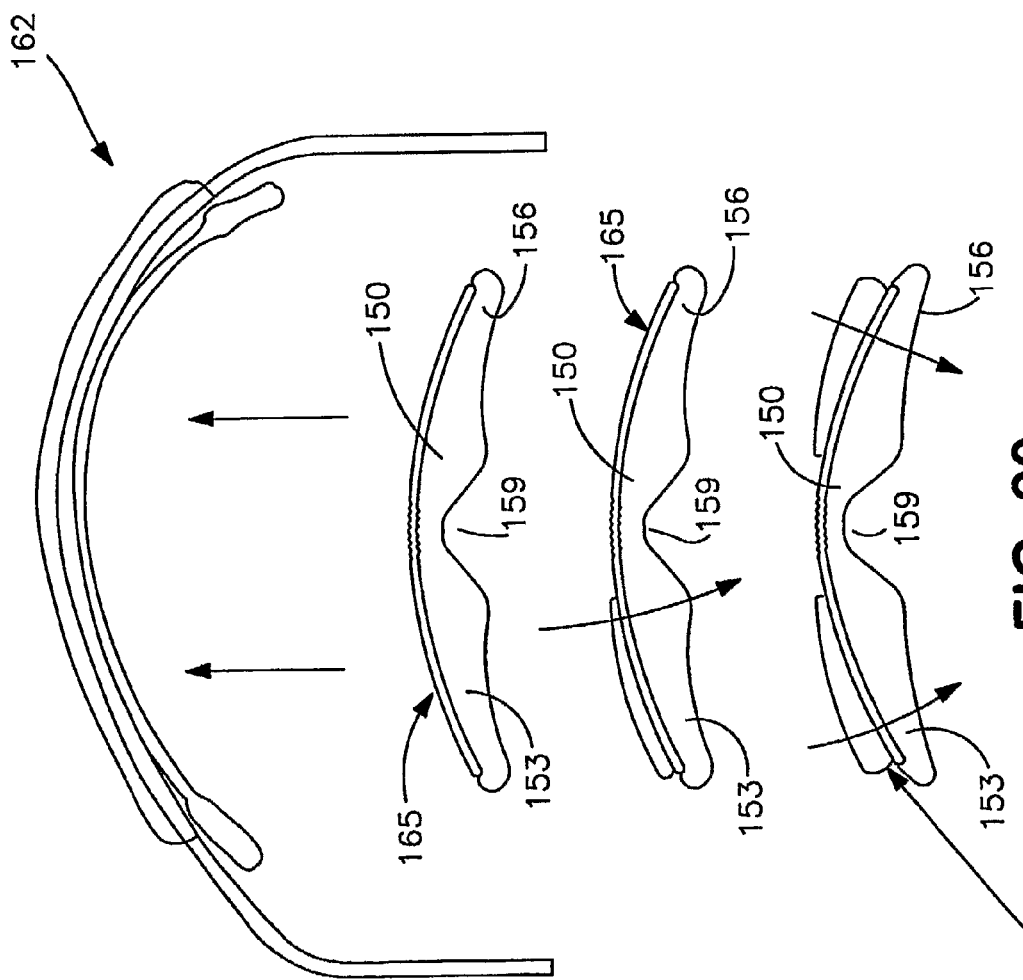
FIG. 20 is a cross sectional view of an orthotic device similar to the orthotic device shown in FIG. 7 illustrating a further embodiment of a segmented tibial liner.

Referring now to FIGS. 20 and 21, a further embodiment of an adjustable tibial liner 150 is illustrated, wherein the attachment of the liner 150 to the ATM back plate, generally referenced at 162, can be similarly accomplished using a VELCRO type fastener system as described above. The adjustable tibial liner 10 preferably includes individually adjustable cam segments 153,156 which define a tibial crest groove 159 there between. FIG. 21 is a cross section view of an orthotic device, including the ATM back plate, i.e. at 162, which may be similar to the tibial cuff portion of the orthotic device illustrated in FIG. 18. As with the preceding embodiment, one layer (not shown) of VELCRO material is affixed to the ATM back plate 162 and a cooperating layer 165 of the VELCRO material is attached to the mating side of the adjustable tibial liner 150.

Each cam segment 153, 156 can be adjustable in the same manner as the cam segments 83, 86 of the tibial liner 80 illustrated in FIGS. 7-11. Additionally, however, as can be seen in the two lower views of the adjustable tibial liner in FIG. 20, the positioning of the cam segments 153, 156 can further be adjusted using chocks 170, i.e., the wedge shaped members illustrated in FIG. 21. The chocks 170 are inserted between the cams 153, 156 and the ATM back plate to further adjust, and maintain, the position of the cam segments 153, 156.

As shown best in FIG. 21, the chocks 170 can be provided in different sizes, and with different angles as shown in the three upper side views of chocks 171, 172 and 173 in FIG. 21. This enables accommodation of varied tibial profiles to customize the fit of the adjustable tibial liner 150, to an individual's anatomy. The chocks 170 can be attached between either or both cams 153. 156 of the tibial liner 150 and the ATM back plate via a VELCRO type fastener arrangement as described previously. As illustrated, one side of the chock 170 has a layer 175 of VELCRO material to attach which cooperates with a mating layer 165 of VELCRO material on the back of the adjustable tibial liner 150. Additionally, the opposite side of the chock 170 has another layer 178 of VELCRO material which cooperates with the layer (not shown) of VELCRO material provided on the ATM back plate.

Referring now to FIGS. 22 and 23, further embodiments of adjustable tibial liners 180 and 190 are illustrated attached to an ATM back plate 188 (shown in cross section). As shown in both FIGS. 22 and 23, the adjustable tibial liners 180 and 190 can be rigidly attached to the ATM back plate 188, for example by a fastener 189, such as a screw or rivet. Each adjustable tibial liner 180, 190 includes individually adjustable cam segments (182, 184 and 192, 194) which define a tibial crest groove (186 and 196) there between.

FIG. 22 illustrates a pair of spacers 187 provided intermediate each cam segment 182, 184 of the adjustable tibial liner 180 and the ATM back plate 188. The spacers 187 can be individually adjusted as to both the position and size thereof to maintain the adjustable tibial liner 180 in a particular position, or configuration, after initial adjustment.

As shown in FIG. 23, pneumatic elements 197 could also be provided instead of, or in combination, with spacers. The pneumatic elements 197 are positioned intermediate each cam segment 192, 194 of the adjustable tibial liner 190 and the ATM back plate 188. The pneumatic elements 197 can be individually inflated, and deflated, to adjust the shape of the liner 190, and/or the positioning of each cam segment 192, 194 to provide individualized fit and activity-specific levels of tibial control, as described previously in regard to other embodiments of the adjustable tibial liner.

As can be seen from the foregoing, the invention provides a segmented and/or adjustable lining for an orthotic device, including various functional elements which provide a number of different advantages. One advantage is grip, both in terms of gripping the soft tissue of the user in to enable the device to function effectively, and also to be able to provide skeletal grip in some situations where this may be advantageous, such as, for example, at the tibia.

The invention has advantages in relation to skin, skincare and general fit. Since each segment is raised, there are spaces between segments and this allows air to circulate. General fit is improved because the segments allow variations in the contour of the user's body to be accommodated. Furthermore, because the segments effectively provide a non-contiguous surface to the skin of a user, movement of soft tissue, such as muscle, adjacent to one segment is less likely to affect the contact of another segment with the body of the user. Accordingly, a more secure fit is achieved.

Another advantage is the addition of Electrophysical Modality to each or all of the discrete segments for therapeutic benefit to the user, as described above.

Yet another advantage is that the segments tend to keep the support structure, or least edges of the support structure, away from the user's skin. This assists in reducing irritation of the users skin by the relatively more rigid support structure.

Where in the foregoing description, reference has been made to specific components or integers of the invention having known equivalents then such equivalents are herein incorporated as if individually set forth. While specific embodiments of the invention have been shown in the drawings and described in detail it will be appreciated by those skilled in the art that various modifications and alternatives would be developed in light of the overall teachings of the disclosure. Accordingly, the particular arrangements disclosed herein are meant to be illustrative only and not limiting as to the scope of the invention, which is to be given the full breadth of the appended claims and in any and all equivalents thereof.

What is claimed is:

1. A knee brace comprising:
   a support member having an upper cuff portion and a lower cuff portion, the upper cuff portion adapted to be secured adjacent a thigh of a user, and the lower cuff portion adapted to be secured about a tibia of the user, the upper cuff portion or the lower cuff portion having a back plate;
   a hinge connecting the upper cuff portion and the lower cuff portion, the hinge located proximate to the knee joint of the user; and
   a resilient liner having a plurality of discrete liner segments, wherein at least one of the plurality of discrete liner segments is adapted to conform to the body portion of the user to which the support member is secured, and wherein at least one of the plurality of discrete liner segments is attached to the back plate;
   wherein at least one of the plurality of discrete liner segments attached to the back plate has an adjustable shape,
   wherein at least one of the plurality of discrete liner segments further comprises a pair of individually adjustable segment portions, and
   wherein the pair of adjustable segment portions comprises a pair of cam portions defining a tibial crest groove therebetween, the pair of cam portions being individually adjustable on either side of the tibial crest groove to conform to a particular shape of the user's tibia and/or maintain the tibia in a desired position.

2. The knee brace of claim 1 wherein the back plate comprises a receptacle formed therein, and wherein at least one of the plurality of discrete liner segments has an attachment member removably received in the receptacle.

3. The knee brace of claim 1 wherein the pair of cam portions is individually movable in a direction in toward the user's tibia, and a direction out away from the user's tibia.

4. The knee brace of claim 1 further comprising a spacer provided intermediate to at least one of the pair of adjustable segment portions and the back plate.

5. The knee brace of claim 4 wherein the spacer comprises a wedge shaped chock.

6. The knee brace of claim 5 wherein the chock is removably securable between at least one of the pair of adjustable segment portions and the back plate.

7. The knee brace of claim 4 wherein the spacer has an adjustable size.

8. The knee brace of claim 7 wherein the spacer is inflatable and/or deflatable to provide the adjustable size.

9. The knee brace of claim 1 wherein at least one of the plurality of discrete liner segments comprises an electrode portion operably connected to a source of electrical power to impart therapeutic stimulation to an associated body portion of the user.

10. The knee brace of claim 1 wherein the support member is semi-rigid.

11. The knee brace of claim 10 wherein the support member comprises a thermoplastic material and a deformable metallic material such that the support member is generally conformable to a leg of the user.

12. The knee brace of claim 1 wherein at least one of the plurality of discrete liner segments comprises a micro-porous waterproof cover material contacting the body portion of the user.

13. The knee brace of claim 1 wherein at least one of the plurality of discrete liner segments conforms to the shape of a thigh and a calf of the user as the knee brace is secured to the user.

14. The knee brace of claim 1 wherein the upper cuff comprises a first strap for securing the upper cuff to a thigh of the user and the lower cuff comprises a second strap for securing the lower cuff adjacent to a calf of the user.

15. The knee brace of claim 1 wherein at least one of the plurality of discrete liner segments is removable, and the at least one removable liner segment is adapted to be secured between at least one of the upper cuff and a thigh of the user and the lower cuff and a calf of the user.

* * * * *